United States Patent [19]

Der Estephanian et al.

[11] 4,019,508
[45] Apr. 26, 1977

[54] WEARABLE, SELF-CONTAINED FULLY MOBILE PERSONAL BREATHING APPARATUS FOR SURGEONS AND OPERATING ROOM PERSONNEL

[75] Inventors: Estephan Der Estephanian, Altadena; Robert E. Foreman, Santa Ana; Robert D. Scott, West Covina; Odd Friis, Huntington Beach, all of Calif.

[73] Assignee: Research Development Systems, Inc., Pasadena, Calif.

[22] Filed: May 21, 1976

[21] Appl. No.: 688,734

[52] U.S. Cl. .............................. 128/142.7; 128/139; 128/142.6; 128/142.5

[51] Int. Cl.² ........................................ A62B 7/02

[58] Field of Search ............ 128/139, 142.5, 142.6, 128/142.7, 145 R, 140 R, 141 R, DIG. 15, 146.6, 142 R, 188; 2/171.3, 14 N

[56] References Cited
UNITED STATES PATENTS

| | | | |
|---|---|---|---|
| 405,850 | 1889 | Rollins | 128/142 R |
| 3,525,334 | 8/1970 | Braman | 128/142.5 |
| 3,955,570 | 5/1976 | Hutter | 128/139 |

*Primary Examiner*—Robert W. Michell
*Assistant Examiner*—Henry J. Recla
*Attorney, Agent, or Firm*—Louis J. Bachand

[57] ABSTRACT

Wearable, self-contained and fully mobile personal breathing apparatus adapted to be worn by a surgeon or other operating room personnel is provided. The apparatus controls contamination of operating room spaces generated by the air normally expired by the wearer during surgery. The apparatus comprises a vest, a high efficiency particulate air filter secured to said vest, and conduit means for capturing and directing contaminated exhaled air from the wearer through the upstream side of said filter and a blower connected to the downstream side of said filter for inducing air flow in the conduit means and through the filter for decontamination and return to the operating room space.

19 Claims, 8 Drawing Figures

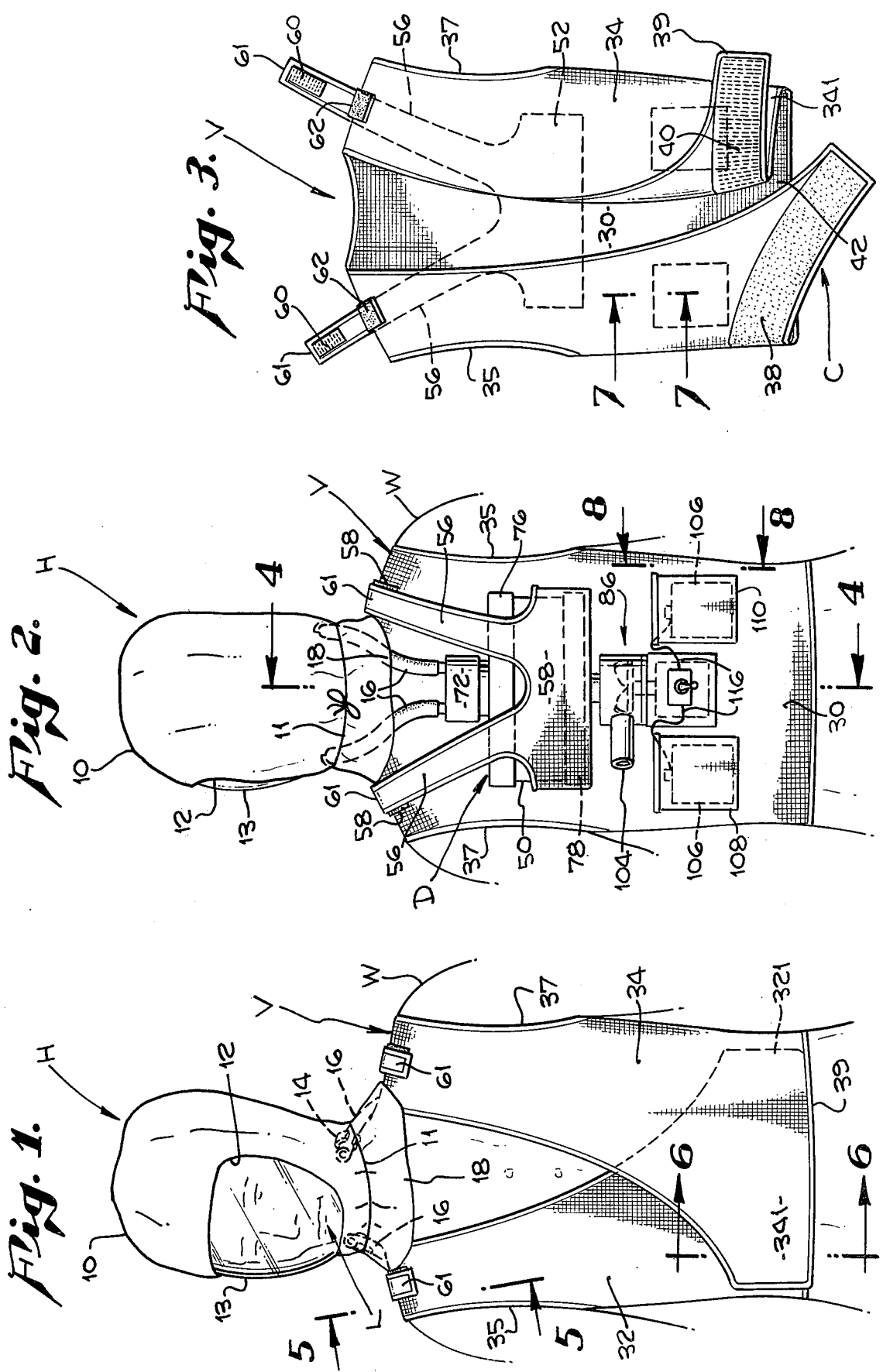

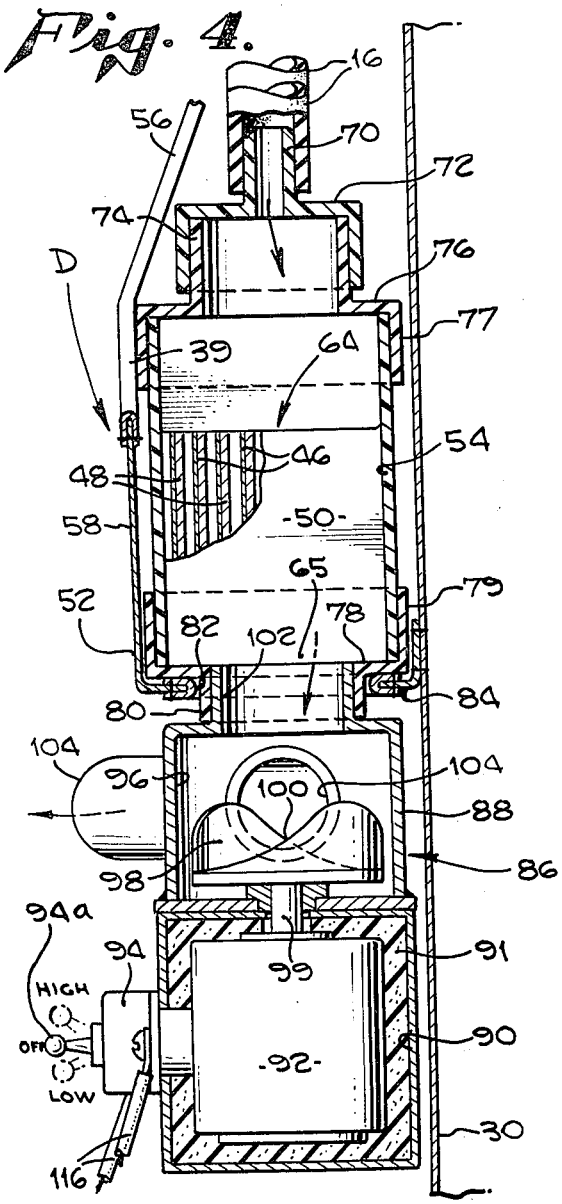
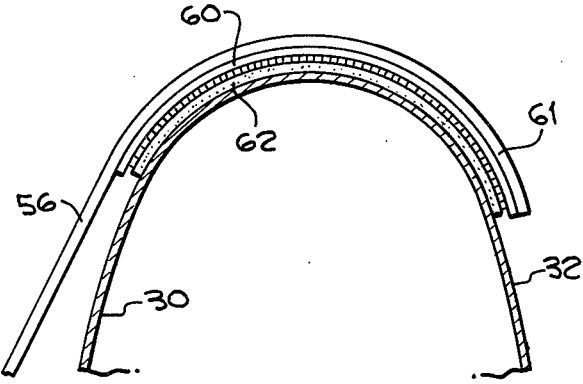
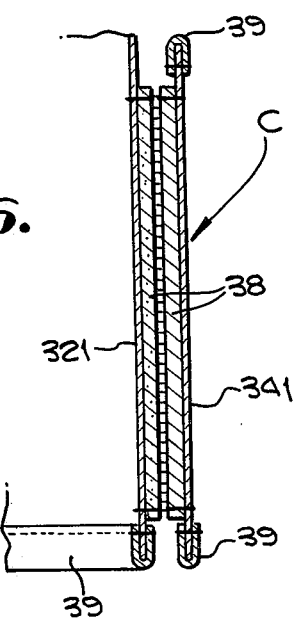
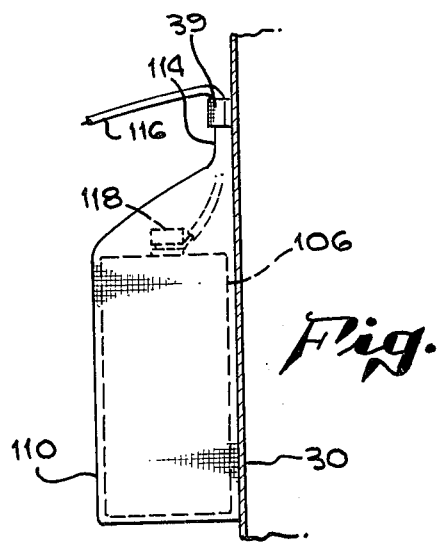
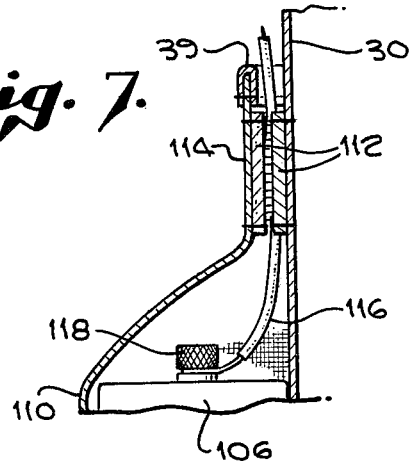

WEARABLE, SELF-CONTAINED FULLY MOBILE PERSONAL BREATHING APPARATUS FOR SURGEONS AND OPERATING ROOM PERSONNEL

BACKGROUND OF THE INVENTION

This invention has to do with prevention of contamination of operating room spaces during surgery, and more particularly with apparatus for controlling contamination having its source in air expiration by surgeons and like health professionals. In a specific sense the invention comprises apparatus for the capture, decontamination, and return of expired air to an operating room, in a convenient effective manner, while preserving the freedom of movement, ease of respiration, and fullness of vision deemed essential to surgeons and the like during surgery.

For the mentioned purposes the invention in general provides a wearable, self-contained and fully mobile apparatus which captures, decontaminates, and returns surgeon-expired air to operating room spaces, against contamination of those spaces by such expired air.

PRIOR ART

As soon as it became apparent that health professionals, although scrubbed, were themselves sources of infection in operating room spaces, steps were taken to insulate the patient from this hazard. Early efforts involved masks and other health screening devices, and devices originally conceived of to protect the doctor from the patients' diseases were adapted to a reverse role. For example, in U.S. Pat. No. 405,850 issued in 1889 to Rollins, a protective, germicidal filter was interposed between the working environment and the doctor, to protect the doctor from communication of patients' diseases. Fresh air was pumped into the enclosed space surrounding the doctor and then out, air conditioning the space and carrying air expired by the doctor in normal respiration out into the room.

More recently, in connection with the protection of delicate or critical electronic and like assemblies, during production, from contamination by workers, "clean" rooms have been devised and workers' bodies have been isolated by air streams and/or suiting against emitting contaminants onto production parts. See, for example, U.S. Pat. No. 3,525,334 issued Aug. 25, 1970, to Scott and Braman.

Concurrently with "clean" room activities, operating rooms were being critically evaluated for their contribution to post-operative infections and loss of or injury to operative patients. Technology of clean rooms was adapted to the problems presented by operating rooms. In highly successful rooms, banks of high efficiency particulate air filters, "hepa" filters, are used to filter all air entering the room, purifying the same by removal of all contaminant particles down to 0.1 micron, with 99.99 percent efficiency. Such installations have reduced all possible sources of patient contamination other than the health professionals and equipment in the room. To further reduce the chance of cross-infection, aspirators have been used in lace of the more traditional surgical masks, e.g., as supplied by Sterilaire Medical Inc. These aspirators include a visor and hood arrangement like that used herein coupled by flexible conduit to vacuum outlets built into the walls of the operating room, akin to a central vacuum system. Conduit inlets in the vicinity of the mouth, i.e., the locus of breath expiration, draw the breath by virtue of the reduced pressure within the conduit away from the doctor and out of the room.

While protection is maximized with the Sterilaire system, the need to be coupled to the wall is irksome to some doctors, and in major surgery the welter of hoses of the numerous persons about the operating table limits the mobility of all persons and hazards tripping or stumbling.

SUMMARY OF THE INVENTION

It is accordingly an object of the invention to provide the maximum in effective patient protection in operating room spaces while freeing doctors and other health professionals from their tether to a vacuum outlet in the room wall. It is a further object to provide a personal, fully mobile and self-contained expired air decontaminating apparatus which the doctor can carry about conveniently and without limits on his movement. It is still further object to provide health care apparatus which is convenient to wear, effective in use, low in cost, regenerable, totally mobile, and attractive, all to the purpose of enabling doctors and all other health professionals to readily afford their patients the maximum in protection during surgery.

The foregoing and other objects of the invention to become apparent hereinafter are realized in accordance with the present invention through the provision of a wearable, self-contained and fully mobile personal breathing apparatus adapted to be worn by a surgeon or like operating room wearer to control contamination of operating room space by the air normally expired by such wearer during surgery, the apparatus comprising: vest means adapted to fit closely about the upper body of the wearer; and a wearer-expired-air-decontaminating means including a vest-supported expired air decontaminating high efficiency particulate air filter, the filter being adapted to remove from the expired air entering the filter upstream side 99.9 percent of all particulate contaminants therein above 0.1 micron in size and arranged to return air thus decontaminated to the operating room space from the downstream side of the filter, and means capturing wearer-expired air at its locus of expiration in locus unconfining relation for air filter passage, the capturing means including conduit communicating the locus with the upstream side of the filter, and a blower inducing expired air flow in said conduit and through said filter in decontaminating relation.

In particular aspects, the apparatus includes a vest comprising a rear portion generally covering the wearer's back, and left and right hand front panels extending forwardly from the rear portion at least partly across the front of the wearer, the front panels carrying at their opposed edge margins cooperating friction elements coupling said panels together. The mentioned friction elements may comprise elongated normally horizontal bands of press-responsive, universally interlocking fiber structure, the bands being in opposed relation and adapted for greater or less longitudinal overlap in interlocked relation to correspondingly adjust the waist dimension of the vest. The vest rear portion further may define a pouch having a top opening and a bottom opening, the pouch being sized to receive the filter with the filter upstream side open to the pouch top opening and the filter downstream side open to the pouch bottom. The apparatus further may include top cover structure defining an inlet to the filter upstream side, bottom cover structure defining an outlet from the filter downstream, the blower being mounted to maintain a pressure differential between said inlet and outlet for inducing expired air passage through the filter. Additionally there may be provided a blower housing for the blower, and means coupling the housing to the filter bottom cover in blower and filter communicating relation through the bottom cover outlet. The blower typically is provided with a chemical cell power supply, the vest rear portion then defining pocket means sized to receive the chemical cell blower power supply in supporting relation. In such embodiments, the apparatus may further include cooperating frictionally responsive elements adapted and arranged to selectively close the pocket means in chemical cell retaining relation.

Also, the mentioned pouch may extend outwardly from the vest rear portion and the apparatus further include strap means extending upwardly from the outer wall of the pouch and cooperating frictionally responsive elements on the strap means and the vest above the pouch to adjustably support the pouch in filter-received relation.

In highly preferred embodiments, the herein disclosed wearable, self-contained and fully mobile personal breathing apparatus employs an air capturing means which includes a face plate supporting the conduit in a manner guiding expired air at its locus of expiration to said conduit, the face plate being supported on the wearer's head. In such embodiments then, there is provided the vest which comprises a rear portion, and overlapping front left and right hand panels connected thereto in arm-hole defining relation; and including also cooperating friction elements on opposed edge margins of the front panels securing the panels together in the worn condition of the vest. There is further provided an air filter receiving pouch formed centrally of the vest rear portion, the pouch being open at the top to receive the air filter, upstream side up, and apertured at the bottom opposite the air filter downstream side and a blower housing communicating the blower inlet with the filter downstream side through the apertured pouch bottom, the conduit being communicated with the filter upstream side whereby expired air from the locus of expiration is blower induced to pass through the filter for decontamination. Strap means is further provided extending upward from the outer wall of the pouch means, cooperating friction elements being provided on the strap means and the vest in opposed relation to vertically support the pouch and filter therein. A chemical cell power supply is provided for the blower and a pocket means are formed on the vest adapted to receive power supply chemical cells in supporting relation, and cooperating friction elements may be provided for the pocket means to retain the chemical cells therein. The mentioned cooperating friction elements typically comprise elongated bands of press-responsive, universally interlocking fiber structure adapted to engage in varying adjustments.

In particular embodiments the apparatus further includes conductive wire electrically connecting the blower motor and the power cells and switch means along said wire controlling operation of the blower motor.

As in earlier described embodiments the apparatus in this embodiment may include pocket means below and laterally spaced from the pouch means, and the pouch support strap means may further comprise two laterally straps respectively extending over each shoulder of the wearer for friction engagement with the vest portion there.

BRIEF DESCRIPTION OF THE DRAWINGS

The invention will be further described as to an illustrative embodiment in conjunction with the attached drawings, in which:

FIG. 1 is a front elevation view of the apparatus in the worn condition;

FIG. 2 is a rear elevation view thereof;

FIG. 3 is a front elevation view of the apparatus vest, partly unfolded and opened;

FIG. 4 is a vertical section taken on line 4—4 in FIG. 2;

FIG. 5 is a detail sectional view taken on line 5—5 in FIG. 1, and somewhat enlarged;

FIG. 6 is a detail sectional view taken on line 6—6 in FIG. 1, and somewhat enlarged;

FIG. 7 is a detail sectional view taken on line 7—7 in FIG. 3, and somewhat enlarged;

FIG. 8 is a view taken on line 8—8 in FIG. 2.

DESCRIPTION OF THE PREFERRED EMBODIMENTS

With reference now to the drawings in detail, in FIGS. 1 and 2 the present apparatus is shown on wearer W to include headgear to capture expired air, generally indicated at H, and vest means generally indicated at V, supporting the expired air decontaminating means D. As will be evident from FIGs. 1 and 2, the entire apparatus is compact, wearable, self-contained and fully mobile. Specifically, the prior art "umbilical cord" of conduit connecting the surgeon to a wall outlet is eliminated.

A highly preferred form of apparatus is shown in the drawings; other arrangements of parts including alternative vest V designs, inversion of the filter part of decontaminating means D, reversal of component locations, and different headgear H can be used within the scope of the present invention providing the criteria set out herein for a successful apparatus as observed.

The headgear H broadly comprises an air impervious paper, plastic or fabric hood 10, having a drawstring closure 11 and a front opening 12. In the opening 12 a face plate 13 suitably fabricated of acrylic plastic and dished as shown to conform broadly to the facial contour of the wearer W is fitted in air blocking relation supported by means not shown in the operative position depicted. The function of the face plate 13 is to permit full vision while defining at L a locus for capture of air expired from the nose and mouth of the wearer W.

Detent clips 14 are carried by hood 10 laterally and below the mouth of wearer W at the locus L. Dual conduits 16 detented in clips 14 lead backward and downward under skirt 18 of hood 10 for the purpose of conveying expired air concentrated by and guided to the conduit by the configuration and location of face plate 13 from the locus of expiration L to decontamination apparatus D, as will be further explained hereinafter.

Continuing with a description of the general arrangement of parts, the vest V is seen to comprise a rear portion 30, and left and right (as worn) front portions 32, 34 respectively which are secured to the rear portion and may be integral, tapering continuations thereof, in either case defining arm-holes 35, 37 with the rear portion as shown through which the arms of wearer W extend. The front panels 32, 34 along their opposed lower edge margins 321, 341, trimmed like other portions of the vest V with piping 39, are provided with a closure means C illustrated to be bands or lengths of Velcro (registered trademark) or like cooperating friction elements, 38 which are press-responsive interlocking fiber structures adapted to engagement variously along their mutual extents to correspondingly vary the waist size or circumference 42 of the vest V, lending universality of fit to the vest, see FIG. 6. Snap or button fasteners may also be used.

Supported by the vest V and coupled to the headgear H by the conduit 16 is the decontamination apparatus per se, best shown in FIG. 4 to include a high efficiency particulate, replaceable air filter 50 of a type known as such, referred to in the trade as a hepa filter and characterized by its ability to filter from an air stream 99.9 percent and more of particulate contaminants of 0.1 micron or more in size. In general, the filter 50 is comprised of an accordion pleated filtering web 48, e.g., of massed glass fibers, separated by fluted light metal separators 46 and transversely tightly pressed in a suitable frame 54. The filter 50 is supported on the rear portion 30 of the vest V, specifically by the pouch 52, which as shown bellies outward from the vest rear portion in filter frame 54-receiving relation; straps 56, laterally separated and vertically directed act to hold the outer wall 58 of the pouch 52 up against the filter weight, the straps themselves extending divergingly therefrom to and slightly over the shoulder curvature to the wearer W, there is to be fastened by interengagement of the frictional surfaces 60 of their end portions 61 with cooperating frictional pads 62 suitable secured to the vest V by means not shown, to anchor the straps adjustably to the vest, see FIGS. 3 and 5. The cooperating frictional surface pad interengagement can be and desirably is provided by a Velcro fastener, as shown, or snap or button arrangement.

As noted above, the present personal breathing apparatus has for its purpose the decontamination of air exposed by surgeons and like health professionals by passage through a high efficiency or hepa filter and then the return of thus decontaminated air to the operating room.

The expired air is localized at the mouth of the wearer and captured by a partial vacuum developed in conduit 16, conveyed by the conduit to and through the filter. Directing our attention now to the air flow induction and air processing portion of the apparatus, the conduits 16 extend from under hood skirt 18 down the back of the wearer W and are sealably fitted onto inlet nipples 70 of manifold 72. Manifold 72 in turn sealably overfits inlet port 74 of top cover 76. Cover 76 is provided with a downwardly extending generally rectangular flange 77 which snugly interfits with filter frame 54. Sealing gaskets, O-rings and like sealing aids (not shown) may be employed at sealing surfaces on the top and bottom of the filter. The arrangement of conduits 16, manifold 72 and top cover 76 provides a highly leak-free path from locus L to the upstream side 64 of the filter 50.

At the downstream side 65 of filter 50 bottom cover 78 is provided, generally configured like top cover 76 to correspondingly have flange 79 snugly interfit the filter frame 54, and to define an outlet port 80, which extends through central aperture 82 in bottom wall 84 of pouch 52.

Below and supported by the filter bottom cover 78 there is provided blower 86 comprising housing 88 having a lower chamber 90 lined with sound deadening foam 91 surrounding electric motor 92 and provided with switch means 94 extending through the chamber wall and form for motor operations control; and upper chamber 96 enclosing a centrifugal fan 98 carried on motor driven shaft 99 and having a central inlet or "eye" 100 below and in registry with outlet pot 80 of bottom cover 78 through neck portion 102 of housing 88 which couples the housing to the bottom cover for support. The output of fan 98 is exhausted through exit tube 104 into the operating room (arrow).

Being so arranged, the blower 86 draws or induces air flow across the filter 50 through conduit 16 from the locus of expiration L and when the air is thereby filtered and forces the same back into the operating room, decontaminated and safe.

A power supply to the blower 86 is provided in the form of chemical cells or batteries 106 received in pockets 108, 110 on the vest portion 30, below, and laterally of the pouch 52, as shown, and enclosed by suitable, e.g., Velcro, fasteners 112, at the top edge margin 114 of the pockets. See FIGS. 7 and 8. Lead wire 116 connects terminals 118 of the chemical 106 to the blower 86 through switch 94 having off, high, and low speed positions to power the blower correspondingly. The wire may be secured to the vest rear portion along its course by a suitable means such as commensurate Velcro fastener, the wire laying between cooperating friction element extents, neatly out of the way and thus protected from catching on equipment and instruments.

OPERATION

Thus described, the vest V is donned by a surgeon or other health professional with the filter 50 in place in pouch 52, the batteries or chemical cells 106 in pockets 108, 110 and these items held in place by appropriate adjustment of the, e.g. Velcro, fastening elements 38, 40, 60, 62, 112. When protection against infections is needed, toggle 94a of switch 94 is thrown to an operative position, e.g., connecting one (low speed) or both (high speed) sets of cells 106 to the blower motor 92. Fan 98 operation results inducing air flow through filter 50 and conduits 16 from locus L, whereby air exhaled by the surgeon is withdrawn by an induced vacuum or negative pressure of 0.1 to 0.2 inches of Hg., into conduits 16 for passage along the conduits, through manifold 72, top cover 76, and filter 50 through the channels defined by pleats of web 48, whereby particulate contaminants are removed from the air stream, into fan eye 100 and thence under positive air pressure out exit tube 104 into the operating room.

Importantly, the purifying, decontaminating filtration is accomplished right at the filter 50 and long hoses tied to remote vacuum-filter systems are not required, when using the present invention. The air passing filter 50 is immediately returned to the operating room space, but decontaminated. Air decontamination is thus effected in a low cost, efficient manner employing small filter elements, small motors, and a minimum of hardware and clothing.

We claim:

1. A wearable, self-contained and fully mobile personal breathing apparatus to be worn by a surgeon or like operating room wearer to control contamination of operating room space by the air normally expired by such wearer during surgery, the apparatus comprising:

vest means adapted to fit closely about the upper body of the wearer, an expiried-air-decontaminating high efficiency, particulate air filter means for removing from said expired air entering the filter upstream side 99.9 percent of all particulate contaminants therein above 0.1 micron in size, said vest means including means for supporting said filter means, means for capturing wearer-expired air at its locus of expiration in locus unconfining relation and for directing said expired air to the upstream side of said filter means including conduit means communicating said locus with the upstream side of said filter means, and means arranged to return air thus decontaminated to said operating room space from the downstream side of said filter including a blower connected to the downstream side of said filter means inducing expired air flow in said conduit and through said filter in decontaminating relation.

2. Wearable, self-contained and fully mobile personal breathing apparatus according to claim 1 in which said vest comprises a rear portion generally covering the wearer's back, and left and right hand front panels extending forwardly from the rear portion at least partly across the front of the wearer, said front panels carrying at their opposed edge margins cooperating friction elements coupling said front panels.

3. Wearable, self-contained and fully mobile personal breathing apparatus according to claim 2 in which said friction elements comprise elongated normally horizontal bands of press-responsive universally interlocking fiber structure, said bands being in opposed relation and adapted for greater or less longitudinal overlap in interlocked relation, to correspondingly adjust the waist dimension of the vest.

4. Wearable, self-contained and fully mobile personal breathing apparatus according to claim 2 in which said blower is provided with a chemical call power supply and said vest rear portion defines pocket means sized to receive said chemical cell blower power supply in supporting relation.

5. Wearable, self-contained and fully mobile personal breathing apparatus according to claim 1 in which said vest rear portion defines a pouch having a top opening and a bottom opening, said pouch being sized to receive said filter with the filter upstream side open to said pouch top opening and the filter downstream side open to the pouch bottom opening.

6. Wearable, self-contained and fully mobile personal breathing apparatus according to claim 5 including also top cover structure defining an inlet to the filter upstream side, bottom cover structure defining an outlet from the filter downstream side, said blower being mounted to maintain a pressure differential between said inlet and outlet for inducing said expired air through said filter.

7. Wearable, self-contained and fully mobile personal breathing apparatus according to claim 6 including also a blower housing and means coupling said housing to said filter bottom cover in blower and filter communicating relation through said outlet.

8. Wearable, self-contained and fully mobile personal breathing apparatus according to claim 7 in which said blower is provided with a chemical cell power supply, and in which said vest rear portion further defines pocket means sized to receive said chemical cell blower power supply in supporting relation.

9. Wearable, self-contained and fully mobile personal breathing apparatus according to claim 8, including also cooperating frictionally responsive elements adapted and arranged to selectively close said pocket means in chemical cell retaining relation.

10. Wearable, self-contained and fully mobile personal breathing apparatus according to claim 5 in which said pouch extends outwardly from said vest rear portion and including also strap means extending upwardly from the outer wall of said pouch, and cooperating frictionally responsive elements on said strap means and said vest above said pouch to adjustably support said pouch in filter-received relation.

11. Wearable, self-contained and fully mobile personal breathing apparatus according to claim 1 in which air capturing means further includes a face plate supporting said conduit in a manner guiding expired air at its locus of expiration, to said face plate being supported on the wearer's head.

12. Wearable, self-contained and fully mobile personal breathing apparatus according to claim 11, in which said vest comprises a rear portion and overlapping front left and right hand panels connected thereto in arm-hole defining relation, and including also cooperating friction elements on opposed edge margins of said front panels securing said panels together in the worn condition of the vest.

13. Wearable, self-contained and fully mobile personal breathing apparatus according to claim 12, including also an air filter-receiving pouch formed centrally of the vest rear portion, said pouch being open at the top to receive said air filter upstream side up and apertured at the bottom opposite said air filter downstream side.

14. Wearable, self-contained and fully mobile personal breathing apparatus according to claim 13 including also a blower housing communicating the blower inlet with said filter downstream side through said apertured pouch bottom, said conduit being communicated with said filter upstream side whereby expired air from the locus of expiration is blower induced to pass through said filter for decontamination.

15. Wearable, self-contained and fully mobile personal breathing apparatus according to claim 14, including also strap means extending upward from the outer wall of said pouch means, cooperating friction elements being provided on said strap means and said vest in opposed relation to vertically support said pouch and filter therein.

16. Wearable, self-contained and fully mobile personal breathing apparatus according to claim 15, including also a chemical cell power supply for said blower, pocket means formed on said vest adapted to receive power supply chemical cells in supporting relation, and cooperating friction elements for said pocket means to retain said chemical cells therein.

17. Wearable, self-contained and fully mobile personal breathing apparatus according to claim 16, in which said cooperating friction elements comprise elongated bands of press-responsive universally interlocking fiber structure adapted to engage in varying adjustments.

18. Wearable, self-contained and fully mobile personal breathing apparatus according to claim 17, including also conductive wire electrically connecting the blower motor and said cells, and switch means along said wire controlling operation of said blower motor.

19. Wearable, self-contained and fully mobile personal breathing apparatus according to claim 18, in which said pocket means are below and laterally spaced from said pouch means, and in which said pouch support strap means further comprise two laterally separated straps respectively extending over each shoulder of the wearer for friction engagement with the vest portion there.

* * * * *